United States Patent [19]

Yamamuro et al.

[11] Patent Number: 5,130,420

[45] Date of Patent: Jul. 14, 1992

[54] PROCESS FOR THE PRODUCTION OF ALKYL GLYCOSIDE

[75] Inventors: Akira Yamamuro; Toyomi Koike; Hiroki Sawada; Akio Kimura, all of Wakayama, Japan

[73] Assignee: Kao Corporation, Tokyo, Japan

[21] Appl. No.: 494,388

[22] Filed: Mar. 16, 1990

[30] Foreign Application Priority Data

Mar. 17, 1989 [JP] Japan ................... 1-65389

[51] Int. Cl.$^5$ ............ C07H 15/00; C07H 1/00; C07H 3/00; C07H 1/06
[52] U.S. Cl. .................. 536/18.6; 536/18.5; 536/124; 536/127; 536/4.1
[58] Field of Search ........ 536/18.6, 18.5, 124, 536/127, 4.1

[56] References Cited

U.S. PATENT DOCUMENTS

| | | | |
|---|---|---|---|
| 3,547,828 | 12/1970 | Mansfield et al. | 536/4.1 |
| 3,565,885 | 2/1971 | Molotsky et al. | 536/18.6 |
| 3,598,865 | 8/1971 | Lew | 536/18.6 |
| 3,839,318 | 10/1974 | Mansfield | 536/18.6 |
| 4,510,306 | 4/1985 | Langdon | 536/18.6 |
| 4,557,729 | 12/1985 | McDaniel et al. | 536/124 |
| 4,713,447 | 12/1987 | Letton | 536/18.6 |

FOREIGN PATENT DOCUMENTS

| | | |
|---|---|---|
| 92355 | 10/1983 | European Pat. Off. |
| 132043 | 1/1985 | European Pat. Off. |
| 132046 | 1/1985 | European Pat. Off. |

*Primary Examiner*—Johnnie R. Brown
*Assistant Examiner*—Everett White
*Attorney, Agent, or Firm*—Sughrue, Mion, Zinn Macpeak & Seas

[57] ABSTRACT

A process is described for the production of an alkyl glycoside which comprises distilling a higher alcohol in the presence of an alkaline substance, or washing a higher alcohol with an aqueous solution of an alkaline substance, and then reacting the higher alcohol with a sugar or a reaction product of a sugar and a lower alcohol. According to this process, an alkyl glycoside showing an excellent hue can be produced by repeatedly using unreacted alcohol recovered from the reaction mixture in the production of an alkyl glycoside.

8 Claims, No Drawings

PROCESS FOR THE PRODUCTION OF ALKYL GLYCOSIDE

FIELD OF THE INVENTION

This invention relates to a process for the production of an alkyl glycoside. More particularly, it relates to a process for the production of an alkyl glycoside showing an excellent hue.

BACKGROUND OF THE INVENTION

An alkyl glycoside, which is a sugar derivative surfactant which is less irritating than other surfactants. Also, though it is a nonionic surfactant, alkyl glycosides form stable foam per se, and, furthermore, exert a foam-stabilizing effect on other anionic surfactants. These characteristics have made alkyl glycosides highly noteworthy.

Although alkyl glycosides as novel surfactants, have the above-mentioned noteworthy characteristics, it is quite difficult to produce them in the form of a commercially useful product.

An alkyl glycoside is produced by reacting a sugar with an alcohol. During this process, however, it is a most serious problem that various procedures in the process frequently cause deterioration of the hue.

When an alkyl glycoside is to be produced by reacting a higher alcohol with a sugar, in particular, the higher alcohol is generally used in large excess with respect to the sugar. This fact indicates that it is very important to recover and reuse the unreacted higher alcohol from the reaction system in order to more economically produce the alkyl glycoside on an industrial scale.

When the unreacted alcohol is recovered by, for example, distillation from the reacted mixture, which will be called the "recovered alcohol" hereinafter, and is to be used as such in the subsequent production of the alkyl glycoside, however, there is a serious problem that the alkyl glycoside thus formed shows a considerably deteriorated hue.

Several methods have been reported for inhibiting the deterioration of hue in the production of an alkyl glycoside. In the production of an alkyl glycoside through a reaction of a higher alcohol with a monosaccharide, for example, JP-A-59-139397 (the term "JP-A" as used herein means an "unexamined published Japanese patent application") discloses a process wherein said reaction is effected in the presence of an acid catalyst composition comprising an acid catalyst and a reducing agent; European Patent 0132043 discloses a process wherein an acid form of an anionic surfactant is used as a catalyst; and European Patent 0132046 discloses a method wherein the neutralization with an organic base is conducted at the termination of reaction. In the step where the obtained alkyl glycoside is separated from the unreacted and recovered alcohol, furthermore, JP-A-62-192396 discloses a process wherein a viscosity depressant is added, since the high viscosity and poor heat stability of the alkyl glycoside would cause particularly serious deterioration of the hue.

However none of these methods can provide an alkyl glycoside which shows a satisfactory hue when applied to a commercial product in practice. JP-A-61-33193 (corresponding to U.S. Pat. No. 4,557,729) proposes to bleach the finally obtained alkyl glycoside with hydrogen peroxide and sulfur dioxide. However this is not a rather drastic measure, and is accompanied by other problems, such as deterioration with respect to odor and a poor stability upon storage.

The above-mentioned facts clearly indicate that it is necessary to regenerate the recovered alcohol to thereby make its qualities comparable to the unused one with regard to, at least, the causes for the coloration, when the recovered alcohol is to be reused in the production of a fresh alkyl glycoside.

SUMMARY OF THE INVENTION

Under these circumstances, we have conducted extensive studies in order to solve the foregoing problems with respect to the reuse of the recovered alcohol. As a result, we have now found that the deterioration of the hue observed in the reuse of the recovered alcohol is caused by acidic components and furan derivatives, which are formed in the thermal decomposition of, for example, residual reducing sugars, and sugar components, which are entrained during the distillation, in the alcohol recovered from the reacted mixture by, for example, distillation. Furthermore, we have found that these impurities can be efficiently removed by contacting the recovered alcohol contaminated with these impurities with an alkaline substance followed by distillating or water-washing for purifying; and that the hue of the alkyl glycoside produced by using the recovered alcohol thus purified is unexpectedly comparable to that produced by using a non-recycled higher alcohol, thus completing the present invention.

Accordingly, the present invention provides a process for the production of an alkyl glycoside which comprises distilling a higher alcohol in the presence of an alkaline substance, or washing a higher alcohol with an aqueous solution of an alkaline substance, and then reacting said higher alcohol with a sugar or a reaction product of a sugar and a lower alcohol.

DETAILED DESCRIPTION OF THE INVENTION

The higher alcohol to be used in the process of the present invention may be represented by the following formula (I):

$$RO(AO)_nH \tag{I}$$

wherein R represents a straight-chain or branched alkyl, alkenyl or alkylphenyl group having from 6 to 22 carbon atoms;

A represents an alkylene group having from 2 to 4 carbon atoms; and n indicates a mean value and is a number equal to 0 to 5.

Specific examples of the higher alcohol represented by formula (I) include a straight or branched alkanol such as hexanol, heptanol, octanol, nonanol, decanol, dodecanol, tridecanol, tetradecanol, pentadecanol, hexadecanol, heptadecanol, octadecanol, methylpentanol, methylhexanol, methylheptanol, methyloctanol, methyldecanol, methylundecanol, methyltridecanol, methylheptadecanol, ethylhexanol, ethyloctanol, ethyldecanol, ethyldodecanol, 2-heptanol, 2-nonanol, 2-undecanol, 2-tridecanol, 2-pentadecanol, 2-heptadecanol, 2-butyloctanol, 2-hexyloctanol, 2-octyloctanol, 2-hexyldecanol and 2-octyldecanol; an alkenol such as hexenol, heptenol, octenol, nonenol, decenol, undecanol, dodecenol, tridecenol, tetradecenol, pentadecenol, hexadecenol, heptadecenol and octadecenol;

and alkylphenols such as octylphenol and nonylphenol. These alcohols or alkylphenols may be used either alone or a mixture of two or more of them. Further, an alkylene oxide adduct of these alcohols or alkylphenols can be used.

More particularly, the higher alcohol to be used in the present invention is separated from a reaction mixture in the production of an alkyl glycoside. The reaction mixture in the production of an alkyl glycoside can be obtained by a known method. It may be obtained by any known method under known conditions. Examples of known methods include a method wherein a sugar is reacted with a higher alcohol in the presence of an acid catalyst; and also a method wherein a sugar is preliminarily reacted with a lower alcohol (for example, methanol, ethanol, propanol, butanol) to thereby give a lower alkyl glycoside which is then reacted with a higher alcohol, as described, for example, in JP-B-47-24532 (the term "JP-B" as used herein means an "examined Japanese patent publication") (corresponding to U.S. Pat. No. 3,598,865), U.S. Pat. No. 3,839,318, European Patent 092355, JP-A-59-139397, and JP-A-58-189195.

In the present invention, the unreacted higher alcohol may be recovered from the reaction mixture in the production of an alkyl glycoside containing said unreacted higher alcohol by a known distillation procedure. For instance, a common distillation procedure comprising heating under reduced pressure, distillation in a thin film evaporator under reduced pressure or topping with adding a viscosity depressant may be employed therefor, as described, for example, in JP-B-48-10716 (corresponding to U.S. Pat. No. 3,547,828), JP-A-58-194902 (corresponding to U.S. Pat. No. 3,565,885) and JP-A-62-192396.

In the process of the present invention, the higher alcohol thus recovered is distilled in the presence of an alkaline substance or washed with an aqueous solution of an alkaline substance.

The alkaline substance to be used in the present invention may be either an inorganic alkaline substance or an organic alkaline substance. Examples thereof include sodium hydroxide, potassium hydroxide, calcium hydroxide, sodium carbonate, potassium carbonate, calcium carbonate, sodium borohydride, stearylamine, distearylamine, and dimethylstearylamine.

When the distillation is conducted in the presence of an alkaline substance in the process of the present invention, the alkaline substance is added to the recovered alcohol. The resulting mixture may be allowed to stand for 0 to 5 hours while stirring, if required, followed by distillation. The amount of the alkaline substance to be added ranges from 0.01 to 5% by weight, based on the weight of the alcohol, and is preferably from 0.05 to 2% by weight. The alkaline substance may be added either as such or in the form of an aqueous solution thereof. The distillation may be conducted under commonly used conditions (temperature, pressure). In the case of decyl alcohol, for example, the distillation may be conducted at 0.1 to 30 mmHg and 110° to 150° C.

When the recovered alcohol is washed with an aqueous solution of an alkaline substance in the process of the present invention, the concentration of the alkaline substance aqueous solution is not particularly limited. Generally speaking, an aqueous solution of from 0.1 to 50% by weight, and preferably from 0.5 to 5% by weight, may be employed therefor. The higher alcohol washed with the alkaline substance aqueous solution may be used as such. Alternately, it may be neutralized, washed with water or distilled. The distillation or water-washing treatment may be conducted without restriction. That is, it may be conducted either continuously, semi-continuously, or batchwise.

The higher alcohol thus purified is reacted with a sugar or a reaction product of a sugar and a lower alcohol to thereby give an alkyl glycoside showing an excellent hue.

The reaction between the higher alcohol and sugar or a reaction product of a sugar and a lower alcohol may be conducted by any of the above-mentioned known methods.

The sugar to be used in the present invention may be selected from monosaccharides, oligosaccharides, and polysaccharides. Examples of the monosaccharides include aldoses such as allose, altrose, glucose, mannose, gulose, idose, galactose, talose, ribose, arabinose, xylose, lyxose. Examples of the oligosaccharides include maltose, lactose, sucrose and maltotriose. Examples of the polysaccharides include hemicellulose, inulin, dextrin, dextran, xylan, starch and hydrolyzed starch. Among these sugars, monosaccharides are preferably used.

To further illustrate the present invention, and not by way of limitation, the following Examples are given. Unless otherwise indicated, all percentages are by weight.

EXAMPLE 1

(a) 11400 g (72.0 mol) of decyl alcohol, 3240 g (18.0 mol) of anhydrous glucose and 96 g (0.5 mol) of p-toluenesulfonic acid monohydrate were heated and stirred in a 30 liter reaction vessel. After heating to 95° C., the pressure in the reaction system was adjusted to 40 mmHg and thus dehydration was initiated. Then $N_2$ was blown into the reaction mixture at a rate of 0.3 $Nm^3/h$ so as to efficiently remove the water formed during the reaction. After five hours, it was confirmed that the glucose had been completely consumed. Next, the reduced pressure was relieved and the reaction mixture was cooled and neutralized with 20 g of NaOH. After filtering the polysaccharides formed as by-products, 4270 g of the alkyl glycoside was separated from 8460 g of the unreacted alcohol under 0.4 mmHg at 130° C.

(b) To 2030 g of the unreacted and recovered alcohol obtained in the step (a), was added 30 g of a 50% aqueous solution of NaOH. The mixture obtained was distilled under reduced pressure (5 mmHg). Thus 1830 g of the distilled alcohol (b.p.: 105° C.) was obtained.

1140 g (7.2 mol) of the distilled alcohol obtained through the distillation in the presence of the alkaline substance, 324 g (1.8 mol) of anhydrous glucose and 9.6 g (50 mmol) of p-toluenesulfonic acid monohydrate were treated in the same manner as the one described in (a), to thereby provide 457 g of an alkyl glycoside (recovered alcohol: 850 g).

EXAMPLE 2

To 2320 g of unreacted and recovered alcohol as described in Example 1-(a) was added 11.6 g of an aqueous solution of NaOH and sodium borohydride containing 12% sodium borohydride and 42% NaOH. The resulting mixture was distilled under reduced pressure (5 mmHg) to thereby provide 2200 g of the distilled alcohol (b.p.: 105° C.).

1140 g of the above-mentioned distilled alcohol was treated in the same manner as that described in Example 1-(b), to thereby provide 438 g of an alkyl glycoside (recovered alcohol: 856 g).

EXAMPLE 3

To 2000 g of unreacted and recovered alcohol as described in Example 1-(a) was added 200 ml of a 1% aqueous solution of NaOH. The resulting mixture was vigorously stirred at 60° C. for five minutes. After being allowed to stand, the mixture separated into phases. Then the pH value of the mixture was adjusted to neutral with a small amount of p-toluenesulfonic acid. Thus 1998 g of water-washed alcohol was obtained.

1140 g of the alkaline substance containing-water-washed alcohol thus obtained was treated in the same manner as that described in Example 1-(b), to thereby provide 420 g of an alkyl glycoside (recovered alcohol: 840 g).

EXAMPLE 4

To 2000 g of unreacted and recovered alcohol as described in Example 1-(a) was added 20 g of stearylamine. Then the mixture was distilled under reduced pressure (5 mmHg) to thereby provide 1900 g of the distilled alcohol (b.p.: 105° C.).

1140 g of the distilled alcohol thus obtained was treated in the same manner as that described in Example 1-(b) to thereby provide 435 g of an alkyl glycoside (recovered alcohol: 860 g).

COMPARATIVE EXAMPLE 1

1140 g of unreacted and recovered alcohol as described in Example 1-(a) was not treated with an alkaline substance, but was subjected as such to the same procedure as that described in Example 1-(b). Thus 457 g of an alkyl glycoside (recovered alcohol: 850 g) was obtained.

COMPARATIVE EXAMPLE 2

2240 g of the unreacted and recovered alcohol described in Example 1-(a) was distilled under reduced pressure (1 mmHg) to thereby provide 2133 g of the distilled alcohol. 1140 g of the distilled alcohol was subjected to the same recovery and reuse procedure as that described in Example 1-(b). Thus 406 g of an alkyl glycoside (recovered alcohol: 799 g) was obtained.

COMPARATIVE EXAMPLE 3

To 2000 g of unreacted and recovered alcohol as described in Example 1-(a) was added 200 ml of distilled water. The resulting mixture was vigorously stirred at 60° C. for five minutes. When allowed to stand, it separated into phases, to thereby provide 2000 g of water-washed alcohol.

1140 g of the water-washed alcohol was treated in the same manner as that described in Example 1-(b). Thus 430 g of an alkyl glycoside (recovered alcohol: 820 g) was obtained.

TEST EXAMPLE 1

The hues (Gardner) of 50% aqueous solutions of the alkyl glycosides obtained in the above-mentioned Examples 1 to 4 and Comparative Examples 1 to 3 were compared with each other. Table 1 shows the results, wherein a lower Gardner value shows the better hue.

An organoleptic evaluation indicated that the alkyl glycosides produced in Examples 1 to 4 showed no odor and were excellent.

TABLE 1

| Alkyl glycoside | Hue of 50% aqueous solution (Gardner) |
| --- | --- |
| Example 1-(a) | 8 |
| Example 1-(b) | 8 |
| Example 2 | 8 |
| Example 3 | 8 |
| Example 4 | 8 |
| Comparative Example 1 | 14 |
| Comparative Example 2 | 13 |
| Comparative Example 3 | 14 |

Table 1 shows that the present invention provides a process for the production of alkyl glycoside of an excellent hue by repeatedly using the unreacted and recovered alcohol obtained in the production of an alkyl glycoside by treatment with the alkaline substance.

While the invention has been described in detail and with reference to specific embodiments thereof, it will be apparent to one skilled in the art that various changes and modifications can be made therein without departing from the spirit and scope thereof.

What is claimed is:

1. A process for the production of an alkyl glycoside, which comprises distilling a higher alcohol in the presence of an alkaline substance, or washing a higher alcohol with an aqueous solution of an alkaline substance, and then reacting said higher alcohol with a sugar or a reaction product of a sugar and a lower alcohol, and said higher alcohol to be distilled or washed is unreacted higher alcohol obtained by separation from a reaction mixture obtained by reacting a sugar with said higher alcohol, said higher alcohol being represented by the following formula (I):

$$RO(AO)_nH \qquad (I)$$

wherein R represents a straight-chain or branched alkyl, alkenyl or alkylphenyl group having from 6 to 22 carbon atoms;

A represents an alkylene group having from 2 to 4 carbon atoms; and n indicates a mean value and is a number equal to 0 to 5, and said lower alcohol is an alcohol containing 1 to 5 carbon atoms.

2. A process for the production of an alkyl glycoside as in claim 1, wherein said higher alcohol to be distilled or washed is obtained by separation from a reaction mixture obtained by first reacting a sugar with a lower alcohol and then reacting the resulting product with a higher alcohol.

3. A process for the production of an alkyl glycoside as in claim 1, which comprises distilling said higher alcohol in the presence of said alkaline substance prior to reacting said higher alcohol with said sugar or reaction product of said sugar and lower alcohol.

4. A process for the production of an alkyl glycoside as in claim 1, which comprises washing said higher alcohol with an aqueous solution of said alkaline substance prior to reacting said higher alcohol with said sugar or reaction product of said sugar and lower alcohol.

5. A process for the production of an alkyl glycoside as in claim 3, wherein the alkaline substance is present in an amount of from 0.05 to 2% by weight based on the weight of said alcohol.

6. A process for the production of an alkyl glycoside as in claim 4, wherein said higher alcohol is washed with an aqueous solution containing alkaline substance in an amount of 0.5 to 5% by weight.

7. A process for the production of alkyl glycoside as in claim 1, wherein the alkaline substance is at least one compound selected from the group consisting of sodium hydroxide, potassium hydroxide, calcium hydroxide, sodium carbonate, potassium carbonate, calcium carbonate, sodium borohydride, stearylamine, distearylamine and dimethylstearylamine.

8. A process for the production of an alkyl glycoside as in claim 1, wherein said lower alcohol is selected from the group consisting of methanol, ethanol, propanol, and butanol.

* * * * *